(12) United States Patent
Kaltschmidt et al.

(10) Patent No.: US 7,865,225 B2
(45) Date of Patent: Jan. 4, 2011

(54) METHOD FOR IMPLEMENTING A MEDICAL PROCEDURE ON A SUBJECT WITH DIFFERENT MEDICAL APPARATUSES THAT EACH PROCESS PATIENT DATA

(75) Inventors: Rainer Kaltschmidt, Eckental/Brand (DE); Kurt-Ulrich Hellmold, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 1258 days.

(21) Appl. No.: 11/300,912

(22) Filed: Dec. 15, 2005

(65) Prior Publication Data
US 2006/0155191 A1 Jul. 13, 2006

(30) Foreign Application Priority Data
Dec. 16, 2004 (DE) .................. 10 2004 060 581

(51) Int. Cl.
*A61B 5/05* (2006.01)
*B23C 1/12* (2006.01)

(52) U.S. Cl. .................. 600/407; 600/427; 709/212; 709/213; 709/217

(58) Field of Classification Search .............. 600/440, 600/407, 427; 707/1; 700/11, 97; 702/19; 709/212–213, 217; 705/2, 3
See application file for complete search history.

(56) References Cited

U.S. PATENT DOCUMENTS

| 4,653,112 | A | 3/1987 | Ouimette |
| 6,201,983 | B1 * | 3/2001 | Haumann et al. ............ 600/407 |
| 6,581,117 | B1 * | 6/2003 | Klein et al. .................. 710/110 |
| 2002/0065682 | A1 * | 5/2002 | Goldenberg .................... 705/2 |
| 2002/0085026 | A1 | 7/2002 | Bocionek et al. |
| 2003/0126279 | A1 | 7/2003 | Hu et al. |
| 2004/0103169 | A1 | 5/2004 | Nolte |
| 2004/0122790 | A1 * | 6/2004 | Walker et al. ................... 707/1 |

FOREIGN PATENT DOCUMENTS

| DE | 101 14 017 | 9/2001 |
| EP | 1 103 902 | 5/2001 |

* cited by examiner

*Primary Examiner*—Eric F Winakur
*Assistant Examiner*—Katherine L Fernandez
(74) *Attorney, Agent, or Firm*—Schiff Hardin LLP

(57) ABSTRACT

In a method for implementation of a medical procedure on a patient with a first medical apparatus that processes patient data and a second medical apparatus that processes patient data, both apparatuses have interfaces that can be connected with one another for exchange of the patent data. Patient data of the patient is electronically stored in the first apparatus, the interfaces of both apparatuses are connected, the patient data is transferred from the first apparatus to the second apparatus, and the procedure is implemented with the second apparatus.

9 Claims, 1 Drawing Sheet

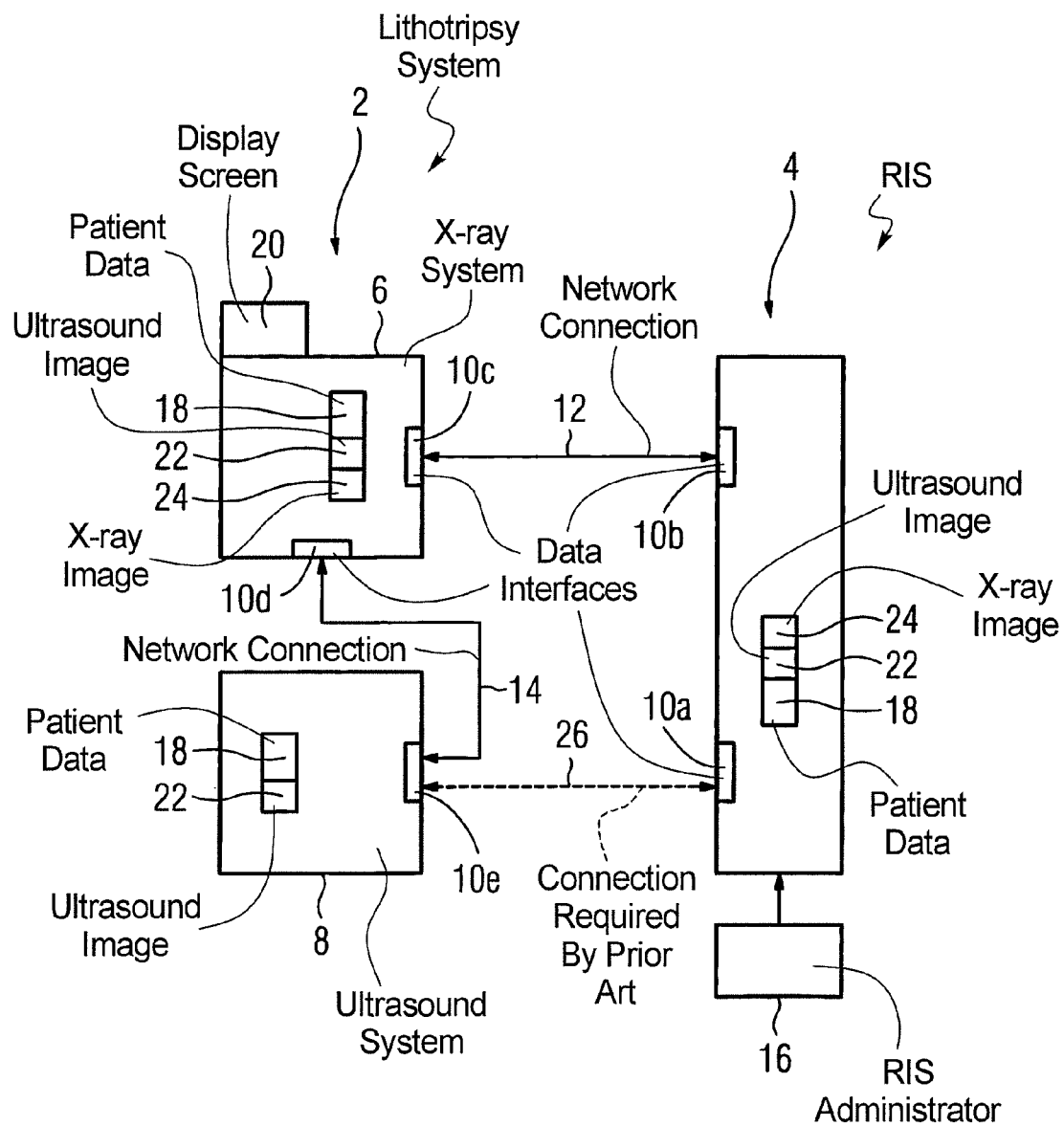

METHOD FOR IMPLEMENTING A MEDICAL PROCEDURE ON A SUBJECT WITH DIFFERENT MEDICAL APPARATUSES THAT EACH PROCESS PATIENT DATA

BACKGROUND OF THE INVENTION

1. Field of the Invention

The present invention concerns a method for implementation of a medical procedure on a patient with a first medical apparatus that processes patient data and a second medical apparatus that processes patient data.

2. Description of the Prior Art

Various medical apparatuses are used today in the implementation of medical procedures on patients. Medical procedures are, for example, examinations, treatments, diagnoses or surgical or interventional operations. For example, x-ray systems, ultrasound apparatuses, computed tomography systems (CT) and magnetic resonance systems (MR) are available as medical apparatuses. The majority of these medical apparatuses operate under computer control, meaning that they are able to process patient data. Such data are, for example, information concerning patients, examination protocols or medical image material archived or acquired in the framework of the medical procedure.

Due to their capability for electronic data processing, such apparatuses are increasingly connected among one another to electronic data networks. The connection today always ensues between a single medical apparatus as a client with a server that, for example, belongs to a hospital information system (HIS) or a radiological information system (RIS).

For their implementation many medical procedures require the use of multiple medical apparatuses. The patient data used in such procedures are sent separately from the HIS/RIS to each individual medical apparatus and thus are also separately administered and stored for each apparatus.

This separation is intricate and elaborate and often hinders the workflow in a medical procedure. Given the use of a number of apparatuses, it is desirable for the user (such as doctors or nursing staff) to be able to also consider and assess examinations or treatments associated with the patient data on site, or to have all associated data in a single data set.

Integrative solutions exist in the field of the DICOM format, a worldwide image format for all imaging medical apparatuses. Multi-modality workstations thus allow the consideration of medical image information at a single workstation, even through the image information was acquired from various apparatuses at various locations, because radiological images are generated from various stationary systems, and the stationary systems are for the most part widely separated from one another.

This known approach still provides no assistance for certain problems, for example, in the case of shockwave lithotripsy in the urological field of expertise. A number of examinations in the framework of a single treatment or assessment for a singe patient are provided or indexed at various apparatuses. Whether and which apparatus or apparatuses is/are actually used is usually decided only upon the actual implementation of the procedure. Especially in lithotripsy, for example, examination is conducted both with x-rays and/or with ultrasound within a single treatment. In order to be able to access all apparatuses as needed, the patient is temporally, separately planned (scheduled) on all apparatuses via the HIS/RIS. If the doctor then uses only one of the two apparatuses, the patient is reported as untreated by the other apparatus. Corresponding corrections in the treatment protocol must be retroactively implemented manually by the HIS/RIS administrator.

The examination results for various processes designated under various treatment identifiers (study ID) are also reported by the individual apparatuses to the HIS/RIS. If the patient is simultaneously treated at both apparatuses, the examination results reported back under separate study IDs must be combined manually to form a single study ID by the HIS/RIS administrator. The accounting according to DRG billing rates is thus made more difficult. The strict separation of the apparatus administration with regard to the HIS/RIS is therefore extremely obstructive for the workflow in the course of a lithotripsy treatment.

Alternatively, the HIS/RIS can schedule the patient only on a single apparatus. Given use of another apparatus, the treating doctor must then register the patient manually. Input errors in the transfer of the patient data from the first to the second apparatus cannot be completely precluded. Moreover, as just mentioned the patient here appears to be duplicated under different study IDs. It additionally occurs that the second associated apparatus, which usually is mobile, requires an additional network connection (in particular DICOM network connection) in the room of the first apparatus. For example, a number of connections, that are then mostly unused, must be made available in a clinic. This entails installation and maintenance costs. Moreover, the second apparatus, as soon as it is added to the procedure, occupies a further logical DICOM node in the HIS/RIS that must likewise be held in reserve in the system.

SUMMARY OF THE INVENTION

An object of the present invention is to improve the implementation of a medical procedure on a patient conducted using a first medical apparatus that processes patient data and a second medical apparatus that processes patient data.

The object is achieved by a method for implementation of a medical procedure on a patient with a first medical apparatus that processes patient data and a second medical apparatus that processes patient data, with both apparatuses having interfaces that can be connected with one another for exchange of the patient data, wherein the patient data of the patient are electronically stored in the first apparatus, the interfaces of both apparatuses are connected, the patient data are transferred from the first apparatus to the second apparatus, and the procedure is implemented with the second apparatus.

The patient data of the patient must only be electronically stored a single time, namely in the first apparatus. The data can either be directly input at the first apparatus or can be stored by a superordinate system, for example a network or storage medium that is accessible by the first apparatus.

Since both apparatuses have interfaces that can be connected with one another for exchange of the patient data and the interfaces of both apparatuses are actually connected, at least one island network composed of the first and second apparatuses is created when neither of the two apparatuses is connected to further data processing apparatuses. The interfaces of both apparatuses can be connected permanently, or only as needed. Of course the connection must exist when both apparatuses are required during a medical procedure.

Because the patient data are transferred from the first apparatus to the second apparatus, input errors to the second apparatus are avoided. Input errors are thus reduced to a minimum given the first input either directly at the first apparatus or in advance given storage of the patient data.

The procedure is implemented at or using the second apparatus, which is supplied with the correct and complete patient data of the appertaining patient due to the transferred data. Patient data can neither be lost nor incorrectly input. A confusion of patients is nearly precluded.

The transfer of the data from the first apparatus to the second apparatus can ensue at any time, for example before or during the implementation of the medical procedure. Even if the individual implementing the medical procedure (for example the treating doctor) initially plans to use only the first apparatus and therefore has stored the patient data to be accessible by the first apparatus, a prior reservation on a specific medical apparatus is thus no longer necessary; the selection of the apparatus can ensue during the medical procedure. The flexibility of the doctor in his apparatus selection is thus distinctly increased.

The medical procedure thus can be begun with the first apparatus and the procedure can be continued with the second apparatus with transfer of the necessary data thereto. Both apparatuses can thus be simultaneously used during the medical procedure, with both apparatuses operating with corresponding or the same patient data.

As noted, patient data can be exchanged between the first apparatus and the second apparatus. During the medical procedure, newly-generated patient data (for example acquired image material) thus can be exchanged between the first apparatus and the second apparatus and still be available in both apparatuses during the medical procedure. Due to the direct connection of the first apparatus and the second apparatus, a detour via an HIS/RIS (which possibly requires intervention of the HIS/RIS administrator) is avoided. The transfer and synchronization of the data between the first apparatus and the second apparatus ensues quickly and in an uncomplicated manner.

After the end of the medical procedure, the patient data can be stored in the first apparatus. Since the data input also occurred at the first apparatus, this represents the server in the island network between the first apparatus and the second apparatus. The hierarchy of both apparatuses is established. All resulting data are thus available at the first apparatus at the end of the treatment. The second medical apparatus thus need not possess data input or output devices whatsoever except for the aforementioned interface. Keyboards and screens thus are not needed or, if present, can be executed simply.

The first apparatus can be operated as a client of the server of a hospital and radiology information system (HIS/RIS). In the first step, the patient data is transferred from the server to the first apparatus. The first apparatus is additionally operated as a sub-server of the HIS/RIS and the second apparatus is operated as a client of the sub-server. Only a single apparatus (namely the first apparatus) appears as a single entity with regard to the HIS/RIS and thus occupies only one logical entry in the system. A patient on whom the medical procedure is to be implemented thus must be individually distinctly registered (scheduled) only on a single apparatus. Only a single treatment identifier (study ID) is thus assigned in the HIS/RIS, which is why the accounting (for example according to DRG rates) according to the implemented procedure is particularly simple upon completion of the overall procedure.

In the island network composed of the first apparatus and the second apparatus, the hierarchical structure is also clearly established given data transfer, since each apparatus is distinctly identified as a server or client. The first apparatus fulfills a double role since it appears as a client with regard to the HIS/RIS and as a sub-server with regard to the second apparatus. The second apparatus occupies no extra archive node in the HIS/RIS.

The sub-server in the first apparatus can simulate the HIS/RIS server. This has the advantage that no change whatsoever is necessary in the second apparatus, whether it is operated through the first apparatus or is independently operated the HIS/RIS in another application. In this case, each second apparatus that can be operated with a standardized HIS/RIS server can be operated through the first apparatus. No additional measures whatsoever are required in the second apparatus.

Alternatively, the sub-server can be provided with a recognizable identifier and so merely has to be entered as a server in the second apparatus in place of the typical HIS/RIS server.

The patient data can be transferred in the data format of the HIS/RIS, a patient to be treated is scheduled only at the first apparatus by the HIS/RIS; the patient can be scheduled at the second apparatus during the procedure. No adaptation whatsoever to the second apparatus is required when it is already prepared for the operation with an HIS/RIS.

An index number can be assigned for the medical procedure. One and the same index number is associated with the first apparatus that processes patient data and the second apparatus that processes patient data. The association of the measures performed respectively by the two apparatuses with a single patient and procedure as well as billing with cost units are significantly simplified.

The first apparatus can be an x-ray imaging system and the second apparatus can be an ultrasound apparatus in which a lithotripsy treatment is implemented as a medical procedure. In lithotripsy there is often a switch between an x-ray image system and an ultrasound apparatus during the treatment without it being known beforehand whether and which apparatuses will be used. In accordance with the inventive method, a lithotripsy is scheduled as a single procedure in the HIS/RIS; the "invisible" change between apparatuses as well as the simplified tracking of the patients and the single invoicing (accounting) represent particularly significant advantages in the medical workflow.

A DICOM Ethernet connection can be used as the interface. DICOM Ethernet connections are particularly simple and can be administered in a standardized manner, can be easily integrated into existing HIS/RIS systems, the data format of the transferred data is standardized, and most medical apparatuses satisfy this standard and thus can be used in the inventive method. The second apparatus then need not be modified when this is already a standard DICOM apparatus. For implementing the method, a first apparatus need only be equipped with a second DICOM Ethernet connection and the corresponding DICOM software must be configured as a server-client software in order to operate the second Ethernet interface as a server.

All image information acquired in the course of the medical procedure can be stored in the x-ray imaging system. The image information can then be shown on the display of the x-ray system. In the medical environment, x-ray image systems usually have the highest-quality monitors that allow a very good assessment of all medical image information. Such monitors must be calibrated, for example, once per half-year. Monitor workstations at x-ray systems are generally optimally set up, for example with regard to the contrast and brightness. Additional information thus often can be learned from ultrasound images display at the x-ray image monitor in comparison to the representation thereof on a comparably lower-quality monitor of the ultrasound apparatus. Assessment and documentation of the overall image material can still be implemented with the highest quality at the site of the scattered radiation system during the measure. Insufficient image material, for example, can be reacquired again on site.

DESCRIPTION OF THE DRAWINGS

FIG. 1 schematically illustrates a lithotripsy system with a radiology information system, operable in accordance with the invention.

DESCRIPTION OF THE PREFERRED EMBODIMENTS

FIG. 1 shows a lithotripsy system 2 and a radiology information system (RIS) 4 that is part of a hospital information system (HIS) (not shown). In addition to a lithotripter (not shown), the lithotripsy system 2 has an x-ray system 6 and an ultrasound system 8 for medical imaging.

The entire system shown in FIG. 1 is networked via a network according to the DICOM standard. For this purpose, both the lithotripsy system 2 and the RIS 4 are provided with Ethernet interfaces 10a-10e. The RIS 5 hereby acts as a server at the interfaces 10a, 10b, whereby the x-ray system 6 is connected at the server's interface 10b as a client via the interface 10c and the network connection 12.

In the following, the lithotripsy treatment of a patient (not shown) is described using FIG. 1. The administrator 16 of the RIS 4 initially enters the details of the patient to be treated into the RIS 4 as patient data 18. In the patient data 18, the administrator 16 moreover notes the point in time at which the lithotripsy treatment should be implemented on the patient and reserves the x-ray system 6 for the appertaining lithotripsy for this time span. In other words, the patient is scheduled on the x-ray system 6.

Shortly before the beginning of the treatment, the patient data 18 are transferred to the x-ray system 6 via the network connection 12. Patient name, previous findings and other data appear as patient data 18 on the screen 20 of the x-ray system 6. The ultrasound system 8 is still inactive at this point in time.

A doctor (not shown) begins the lithotripsy treatment of the patient and initially uses the x-ray system 6 in order to irradiate the patient and to locate a kidney stone to be disintegrated. The doctor establishes that the stone cannot be located sufficiently well in the patient with the x-ray system 6 and therefore decides during the running treatment to likewise use the ultrasound system 8 for lithotripsy.

The ultrasound system 8 is therefore moved to the patient, is activated, and the ultrasound system 8 is connected with the x-ray system 6 via the network connection 14. The ultrasound system 8 functions as a client. The x-ray system 6 is additionally operated as a server (or, respectively, sub-server subordinate to the RIS 4) with regard to its interface 10d and therewith operates the ultrasound apparatus 8. In the ultrasound apparatus 8, the x-ray system 6 is merely entered as a server instead of the RIS server otherwise typical in the RIS 4. The data connection between x-ray system 6 and ultrasound system 8 can thus be established.

The ultrasound system 8 signs onto the server of the x-ray system 6 via the network connection 14. The doctor hereupon schedules the patient, for example via a simple mouse click on the ultrasound system 8, whereupon the patient data 18 are transferred via the network connection 14 to the ultrasound system 8. The stone to be located is properly recognizable using the ultrasound system 8, which is why the doctor adds the corresponding ultrasound image 22 to the patient data 18. The ultrasound image 22 is transferred over the network connection 14 to the x-ray system 6 and displayed on the high-quality screen 20 there.

The doctor now begins to shatter the stone, and determines that the fragments can no longer be satisfactorily localized with the ultrasound system 8. The doctor continues the treatment with the x-ray system 6, whereupon the doctor likewise appends an x-ray image 24 of the stone fragments to the patient data 18.

After the end of the lithotripsy procedure, the doctor reports the end of the treatment together with the patient data 18 expanded by the ultrasound image 22 and x-ray image 24 to the RIS 4 via the network connection 12. With regard to the RIS 4, the changed or expanded patient data 18 thus receive a single, unambiguous treatment number under which the DRG billing of the lithotripsy treatment ensues later. Although the patient was treated both with the x-ray system 6 and with the ultrasound system 8 and was scheduled at both apparatuses, two separate events do not appear in the RIS 4.

In lithotripsy systems that do not operate according to the invention method, the ultrasound system 8 with its interface 10e is directly connected with the interface 10a of the RIS 4 in parallel with the x-ray system 6. This configuration is shown dashed in FIG. 1 by the network connection 26. X-ray system 6 and ultrasound system 8 are then logically administered on the RIS 4 as two separate apparatuses. The patient data 18 are transferred to both apparatuses. The reports of both apparatuses to the RIS 4, namely the patient data 18 together with the ultrasound image 22 or with the x-ray image 24 are respectively assigned separate treatment numbers. The administrator 16 must subsequently consolidate patient data 18, ultrasound image 22 and x-ray image 24 manually into a single data packet under a single treatment number in the RIS 4 since the conducted lithotripsy is one and the same medical process.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for implementing a medical procedure on a subject comprising the steps of:

designating and reserving a group of medical apparatuses for implementing an entirety of a medical procedure on a subject, said group including a first medical apparatus having a data interface;

electronically storing patient data associated with the subject, needed for implementing said medical procedure, in said first medical apparatus and implementing an initial portion of said medical procedure on said subject with said group including said first medical apparatus;

only after beginning implementation of said initial portion of said medical procedure, identifying a second medical apparatus that is not in said group and that performs a medical function not performed by any apparatus in said group, as being necessary for completion of said entirety of said medial procedure, said second medical apparatus also having a data interface, and connecting said data interface of said first medical apparatus with said data interface of said second medical apparatus, exclusively through a direct connection between said data interfaces that did not exist prior to beginning said implementation of said initial portion of said medical procedure, said second medical apparatus not having said patient data stored therein at a time said direct connection is made;

after making said direct connection, transferring said patient data from said first medical apparatus to said second medical apparatus via the respective data interfaces thereof; and subsequently proceeding with said medical procedure on said subject using said second medical apparatus.

2. A method as claimed in claim 1, comprising generating additional patient data with said second medical apparatus while proceeding with said medical procedure using said second medical apparatus, and exchanging said patient data and said additional patient data in both directions via said data interfaces between said first medical apparatus and said second medical apparatus.

3. A method as claimed in claim 2, comprising upon completion of said medical procedure at said second medical apparatus, electronically storing all patient data associated with said medical procedure at said first medical apparatus.

4. A method as claimed in claim 3, comprising operating said first medical apparatus as a client of a server of an information system selected from the group consisting of hospital information systems and radiology information systems, and wherein the step of electronically storing said patient data in said first medical apparatus comprises transferring said patient data from said server to said first medical apparatus, and operating said first medical apparatus as a sub-server of said information system and operating said second medical apparatus as a client of said sub-server after connecting the data interfaces of the first and second medical apparatuses.

5. A method as claimed in claim 4, comprising transferring said patient data from said server to said first medical apparatus in a data format prescribed by said information system, and scheduling said subject in said information system for treatment only with said group of medical apparatus that includes said first medical apparatus, and scheduling said subject for treatment by with said second medical apparatus after said beginning implementation of said medical procedure.

6. A method as claimed in claim 4, comprising providing said medical procedure with an index number of use in said information system, and associating patient data processed by each of said first medical apparatus and said second medical apparatus with said index number.

7. A method as claimed in claim 1, wherein said first medical apparatus is an x-ray imaging system and wherein said second medical apparatus is an ultrasound apparatus, and wherein said medical procedure is a lithotripsy procedure.

8. A method as claimed in claim 7, wherein said x-ray imaging system comprises a visual display, and comprising electronically storing in said x-ray imaging system, all patient data acquired during said medical procedure, including ultrasound images acquired by said ultrasound apparatus, and visually displaying all of said patient data at said visual display of said x-ray imaging system, including said ultrasound images.

9. A method as claimed in claim 1, comprising employing a DICOM Ethernet connection as each of said interfaces.

* * * * *